United States Patent
Ma et al.

(10) Patent No.: US 10,052,368 B2
(45) Date of Patent: Aug. 21, 2018

(54) PEGYLATED TISSUE KALLIKREIN, AND PREPARATION METHOD THEREFOR AND USES THEREOF

(71) Applicants: ZONHON BIOPHARMA INSTITUTE INC., Changzhou, Jiangsu (CN); GENSUN INSTITUTE OF BIOMEDICINE CO.,LTD., Wujin Changzhou, Jiangsu (CN)

(72) Inventors: Bruce Yong Ma, Jiangsu (CN); Jun Wang, Jiangsu (CN); Jing Qiu, Jiangsu (CN); Dinglong Wu, Jiangsu (CN); Chunlin Xu, Jiangsu (CN); Chen Chen, Jiangsu (CN); Yaofang Wang, Jiangsu (CN)

(73) Assignees: ZONHON BIOPHARMA INSTITUTE INC., Changzhou (CN); GENSUN INSTITUTE OF BIOMEDICINE CO., LTD., Changzhou (CN)

( * ) Notice: Subject to any disclaimer, the term of this patent is extended or adjusted under 35 U.S.C. 154(b) by 36 days.

(21) Appl. No.: 15/109,364

(22) PCT Filed: Jan. 9, 2014

(86) PCT No.: PCT/CN2014/070344
§ 371 (c)(1),
(2) Date: Jun. 30, 2016

(87) PCT Pub. No.: WO2015/100768
PCT Pub. Date: Jul. 9, 2015

(65) Prior Publication Data
US 2017/0049864 A1    Feb. 23, 2017

(30) Foreign Application Priority Data
Dec. 30, 2013    (CN) .......................... 2013 1 0745409

(51) Int. Cl.
| A61K 38/54 | (2006.01) |
| A61K 38/48 | (2006.01) |
| A61K 47/48 | (2006.01) |
| C12N 9/64  | (2006.01) |

(52) U.S. Cl.
CPC .... *A61K 38/4853* (2013.01); *A61K 47/48215* (2013.01); *C12N 9/6445* (2013.01); *C12Y 304/21035* (2013.01)

(58) Field of Classification Search
None
See application file for complete search history.

(56) References Cited

U.S. PATENT DOCUMENTS

| 7,052,686 B2 * | 5/2006 | Lee ..................... C07K 14/5428 424/78.3 |
| 2011/0150781 A1 * | 6/2011 | Charles .............. A61K 38/4853 424/43 |
| 2013/0315891 A1 * | 11/2013 | Charles ................ A61K 9/0019 424/94.64 |

FOREIGN PATENT DOCUMENTS

| CN | 101400363 A | 4/2009 |
| CN | 101108895 B | * 10/2011 |
| WO | 2010/108262 A1 | 9/2010 |
| WO | WO 2013/156488 A2 | * 10/2013 |

OTHER PUBLICATIONS

Machine translation of CN 101108895 B downloaded from ProQuest Dialog on Sep. 28, 2017.*
Schmader et al. Clinical J. Pain (2001) 18: 350-354.*
Yu et al. J. Pharmaceutical Sci. (2010) 99(8): 3326-3333.*
Na et al. AAPS PharmSciTech (2003) 4(4): Article 72, pp. 1-7.*
Tong et al. Int. J. Biol. Macromolec. (2010) 46: 331-336.*
Non-English Search Report dated Sep. 26, 2014 for Application No. PCT/CN2014/070344 with English translation.
espacenet English abstract of CN 101400363 A.
Wang, Xu-dong, et al., "Site-specific PEGylation Strategies and Suitable Modified Sites of Protein Drugs", China Biotechnology,Nno. 4, vol. 30, Dec. 31, 2010, pp. 101-109.
Olsson, A. Y., et al., "glandular kallikrein precursor [Sus scrofa]", GenBank:AAQ23716.1, Jun. 18, 2014, 1 page.
Nakanishi, K., et al., "kallidinogenase", GenBank:2009261A, Nov. 15, 1992, 1 page.

* cited by examiner

*Primary Examiner* — Susan M Hanley
(74) *Attorney, Agent, or Firm* — Buchanan Ingersoll & Rooney PC

(57) ABSTRACT

The present invention relates to polyethylene glycol (PEG) modified protein drugs, and a PEGylated tissue kallikrein, a preparation method and use thereof are disclosed. The tissue kallikrein has a sequence as shown in SEQ ID No. 1 or SEQ ID No. 2, and the tissue kallikrein may be natural or recombinant. The PEG has a molecular weight of 20 to 40 kDa, and is conjugated to the N-terminal primary amino of the tissue kallikrein. In addition to the advantages of significantly extended half-life, significantly reduced immunogenicity and stable and uniform structure, the biological activity of the PEGylated KLK1 provided in the present invention is improved to a higher extent, which is more significant in the treatment of cerebral apoplexy and diabetic nephropathy in particular.

6 Claims, 9 Drawing Sheets

SEQUENCE LISTING

```
<160> NUMBER OF SEQ ID NOS: 8

<210> SEQ ID NO 1
<211> LENGTH: 239
<212> TYPE: PRT
<213> ORGANISM: Sus scrofa

<400> SEQUENCE: 1

Ile Ile Gly Gly Arg Glu Cys Glu Lys Asp Ser His Pro Trp Gln Val
1               5                   10                  15

Ala Ile Tyr His Tyr Ser Ser Phe Gln Cys Gly Gly Val Leu Val Asp
            20                  25                  30

Pro Lys Trp Val Leu Thr Ala Ala His Cys Lys Asn Asp Asn Tyr Gln
        35                  40                  45

Val Trp Leu Gly Arg His Asn Leu Phe Glu Asn Glu Val Thr Ala Gln
    50                  55                  60

Phe Phe Gly Val Thr Ala Asp Phe Pro His Pro Gly Phe Asn Leu Ser
65                  70                  75                  80

Leu Leu Lys Asn His Thr Lys Ala Asp Gly Lys Asp Tyr Ser His Asp
                85                  90                  95

Leu Met Leu Leu Arg Leu Gln Ser Pro Ala Lys Ile Thr Asp Ala Val
            100                 105                 110

Lys Val Leu Glu Leu Pro Thr Gln Glu Pro Glu Leu Gly Ser Thr Cys
```

```
                115                 120                 125
Gln Ala Ser Gly Trp Gly Ser Ile Glu Pro Gly Pro Asp Phe Glu
    130                 135                 140

Phe Pro Asp Glu Ile Gln Cys Val Glu Leu Thr Leu Leu Gln Asn Thr
145                 150                 155                 160

Phe Cys Ala Asp Ala His Pro Asp Lys Val Thr Glu Ser Met Leu Cys
                165                 170                 175

Ala Gly Tyr Leu Pro Gly Gly Lys Asp Thr Cys Met Gly Asp Ser Gly
            180                 185                 190

Gly Pro Leu Ile Cys Asn Gly Met Trp Gln Gly Ile Thr Ser Trp Gly
        195                 200                 205

His Thr Pro Cys Gly Ser Ala Asn Lys Pro Ser Ile Tyr Thr Lys Leu
    210                 215                 220

Ile Phe Tyr Leu Asp Trp Ile Asn Asp Thr Ile Thr Glu Asn Pro
225                 230                 235
```

<210> SEQ ID NO 2
<211> LENGTH: 238
<212> TYPE: PRT
<213> ORGANISM: Homo sapiens

<400> SEQUENCE: 2

```
Ile Val Gly Gly Trp Glu Cys Glu Gln His Ser Gln Pro Trp Gln Ala
1               5                   10                  15

Ala Leu Tyr His Phe Ser Thr Phe Gln Cys Gly Gly Ile Leu Val His
                20                  25                  30

Arg Gln Trp Val Leu Thr Ala Ala His Cys Ile Ser Asp Asn Tyr Gln
            35                  40                  45

Leu Trp Leu Gly Arg His Asn Leu Phe Asp Asp Glu Asn Thr Ala Gln
        50                  55                  60

Phe Val His Val Ser Glu Ser Phe Pro His Pro Gly Phe Asn Met Ser
65                  70                  75                  80

Leu Leu Glu Asn His Thr Arg Gln Ala Asp Glu Asp Tyr Ser His Asp
                85                  90                  95

Leu Met Leu Leu Arg Leu Thr Glu Pro Ala Asp Thr Ile Thr Asp Ala
                100                 105                 110

Val Lys Val Val Glu Leu Pro Thr Gln Glu Pro Glu Val Gly Ser Thr
            115                 120                 125

Cys Leu Ala Ser Gly Trp Gly Ser Ile Glu Pro Glu Asn Phe Ser Phe
        130                 135                 140

Pro Asp Asp Leu Gln Cys Val Asp Leu Lys Ile Leu Pro Asn Asp Glu
145                 150                 155                 160

Cys Lys Lys Ala His Val Gln Lys Val Thr Asp Phe Met Leu Cys Val
                165                 170                 175

Gly His Leu Glu Gly Gly Lys Asp Thr Cys Val Gly Asp Ser Gly Gly
                180                 185                 190

Pro Leu Met Cys Asp Gly Val Leu Gln Gly Val Thr Ser Trp Gly Tyr
            195                 200                 205

Val Pro Cys Gly Thr Pro Asn Lys Pro Ser Val Ala Val Arg Val Leu
        210                 215                 220

Ser Tyr Val Lys Trp Ile Glu Asp Thr Ile Ala Glu Asn Ser
225                 230                 235
```

<210> SEQ ID NO 3
<211> LENGTH: 717

<212> TYPE: DNA
<213> ORGANISM: Homo sapiens

<400> SEQUENCE: 3

```
atcgtcggtg gatgggaatg tgagcaacat tctcagccat ggcaagcagc tttgtaccac    60
ttttccacct tccagtgtgg tggaattttg gttcatagac aatgggtcct tactgccgca   120
cactgcatct ctgataacta tcagttgtgg cttggtagac ataacttgtt tgatgacgaa   180
aatactgccc aattcgttca tgtctcagag agttttccac accctggttt caacatgtct   240
ttgcttgaaa atcatactag acaggctgat gaggactact cccacgattt gatgttgctt   300
agacttacag aaccagccga taccattact gacgcagtta aggttgtcga gttgccaaca   360
caagaacctg aggttggttc aacctgtttg gcttctggtt ggggttctat tgaaccagag   420
aactttagtt tccctgatga cttgcagtgt gttgatttga agatccttcc taatgacgaa   480
tgcaagaaag ctcatgttca aaaagtcaca gatttcatgt tgtgtgttgg tcaccttgaa   540
ggtggaaagg atacctgtgt tggagactct ggtggaccat tgatgtgcga cggtgttctt   600
caaggagtca cttcatgggg ttatgttcct tgcggaacac caaacaagcc tagtgtcgca   660
gttagagtcc ttagttatgt caagtggatc gaagatacaa tcgctgaaaa tagttag      717
```

<210> SEQ ID NO 4
<211> LENGTH: 717
<212> TYPE: DNA
<213> ORGANISM: Homo sapiens

<400> SEQUENCE: 4

```
atcgtcgggg gttgggagtg tgaacagcat agtcagccct ggcaggccgc tctgtaccac    60
ttctccacct ttcagtgcgg cggaatcctg gtgcacaggc agtgggtcct gacagcagcc   120
cattgtatta gcgataacta tcagctgtgg ctgggccggc ataacctgtt cgacgatgag   180
aataccgccc agtttgtgca cgtctcagaa tccttccccc atcctggctt caacatgagt   240
ctgctggaga atcacaccag gcaggctgac gaagattact cacatgacct gatgctgctg   300
cgactgacag agccagcaga cactatcacc gatgctgtga aggtggtcga gctgcccaca   360
caggaacctg aagtgggctc tacttgcctg gcaagcggat ggggttctat cgagcctgaa   420
aacttcagtt ttccagacga tctgcagtgc gtggacctga agattctgcc taatgatgag   480
tgtaagaaag ctcacgtcca gaaagtgact gatttttatgc tgtgcgtggg gcatctggag   540
ggaggcaagg acacctgcgt cggcgactcc ggaggacctc tgatgtgtga cggggtgctg   600
cagggtgtca ctagctgggg ctacgtgcca tgtggaaccc caaataagcc ctccgtggcc   660
gtcagagtgc tgagctatgt gaaatggatc gaggacacca ttgctgaaaa cagttga      717
```

<210> SEQ ID NO 5
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 5

```
gccgctcgag aagagagaag cagaggctat cgtc                                34
```

<210> SEQ ID NO 6
<211> LENGTH: 36
<212> TYPE: DNA
<213> ORGANISM: Artificial sequence
<220> FEATURE:

```
<223> OTHER INFORMATION: Synthetic oligonucleotide

<400> SEQUENCE: 6
aaggaaaaaa gcggccgcct aactattttc agcgat                            36

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
catgcctagg gccaccatgt ccgctctgct                                   30

<210> SEQ ID NO 8
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 8
gggcgtatac tcaactgttt tcagcaatgg t                                 31
```

PEGYLATED TISSUE KALLIKREIN, AND PREPARATION METHOD THEREFOR AND USES THEREOF

RELATED APPLICATION INFORMATION

This application is a 371 of International Application PCT/CN2014/070344 filed 9 Jan. 2014, which claims priority from Chinese Application No.: 201310745409.1 filed 30 Dec. 2013, the content of which is incorporated herein by reference.

REFERENCE TO SEQUENCE LISTING SUBMITTED VIA EFS-WEB

This application includes an electronically submitted sequence listing in .txt format. The .txt file contains a sequence listing entitled "2016-11-02_U_019672-0_ST25.txt" created on Nov. 2, 2016 and is 7,456 bytes in size. The sequence listing contained in this .txt file is part of the specification and is hereby incorporated by reference herein in its entirety.

FIELD OF THE INVENTION

The present invention relates to polyethylene glycol (PEG) modified protein drugs, and in particular to PEG modified tissue kallikrein, a preparation method, and use thereof in the preparation of drugs.

DESCRIPTION OF RELATED ART

Kallikrein, also referred to as kininogenase or kallidinogenase, is one of the serine proteinases, and exists in a variety of tissue and biological fluids, which functions to catalyze the release of a biologically active peptide (kinin) from a macromolecular precursor (kininogen). Kallikrein has the physiological effects of dilating the capillaries and arteries and increasing the permeability, to increase the blood supply to the coronary-arteries, brain, and retina. Kallikrein is useful in the treatment of diseases such as hypertension-related coronary artery disease and arteriosclerosis, and also has therapeutic effects on angina, vasospasm, thromboangiitis obliterans, chilblain and trauma. Also, kallikrein can serve as an activator, to activate the plasminogen into fibrinolysin, and hydrolyze insoluble fibrin into soluble small peptides, thereby exerting a therapeutic effect on cerebral infarction, atherosclerosis, and the like, and being used in the treatment of thrombi and prevention of thrombus reformation (G. M. Yousef, E. P. Diamandis Clin Biochem, 2003(36): 443-452). Vitro studies show that, kallikrein has an ex-vivo dilation effect on arteries, and can inhibit the platelet aggregation, and enhance the deformability and oxygen dissociation ability of hemocyte. Animal experiments show that intravenous injection of kallikrein can increase the blood flow in intervertebral, common carotid and femoral arteries in anaesthetized dogs, and increase the blood flow in posterior limbs of anaesthetized dogs and in muscles of *Oryctolagus cuniculus*. Therefore, kininogenase has a high application value in the treatment of diseases such as human microcirculatory disturbances (for example, diabetic nephropathy or diabetic ocular fundus pathology and the like), and mild to moderate acute thrombotic cerebral infarction.

The existing kallikrein-based drugs available in the Chinese market are divided into two classes. One class includes tissue kallikreins extracted from porcine pancreas, which are widely available, but suffer from a higher immunogenicity, thus being unsuitable for intravenous administration. The other class includes human urine kininogenases extracted and purified from fresh human urine, which have no the problem of immunogenicity, but suffer from great limitations on raw materials, and thus the yield is low. In addition, both of the two classes have the problems of short half-life, and requirement for repeated administration. In order to overcome the ubiquitous disadvantages of poor biostability, short half-life in vivo, presence of immunogenicity, and the like, of such proteins and polypeptides for medical use, the proteins and polypeptides are frequently genetically engineered and chemically modified, to improve the in vivo biostability, extend the half-life, and reduce or eliminate the immunogenicity of the proteins and polypeptides for medical use. However, due to the particular structure of each protein, the applicability of various methods and actual effects generated are significantly different.

Polyethylene glycol (PEG) is a commonly used protein modifier, which can effectively extend the half-life and decrease the immunogenicity of proteinaceous biodrugs. The PEG modification may be random modification and site-directed modification. Random modification refers to a modification reaction performed on a amino of lysine of the protein. This type of PEG modifier reacts quickly and has a high modification rate. However, the modification products are relatively complex, the site of mono-modification in the product is nonuniform, the activity of the modified products are diverse, and the stability among batches is difficult to be ensured. Site-directed modification mainly includes N-terminal modification and modification of cysteine residue, both of which can ensure the consistency of samples, but have a higher requirement for the structure and property of the protein. Also, in most cases, the PEGylated protein drug has a reduced activity as compared with the unmodified original protein, and the activity of the modified protein is generally only 30 to 40%, or even lower, of the original protein. For example, PEG-Intron from Schering-Plough Inc. is interferon modified with PEG having a molecular weight of 5000, and the activity thereof after modification is only 8% of the original protein. Moreover, with the increase of the molecular weight of PEG, the modified protein has a much significantly reduced activity.

For example, after the erythropoietin (EPO) is modified with PEG having a molecular weight of 20 KDa, 30 KDa, and 40 KDa, the activity is significantly reduced with the increase of the molecular weight of PEG (Yin-jue Wang, Journal of Controlled Release, 2010(145): 306-313). It can be seen that the structure of the protein, the molecular weight of PEG, and the site to be modified have a considerable influence on the biological activity of the PEGylated protein. For the modification of a particular drug, the PEG modifier is the most important factor that affects the physicochemical properties, in vivo and in vitro biological activities, pharmacokinetics, pharmacodynamics and clinical manifestations of the modified products.

At present, there is no relevant report on the PEGylation of kininogenase abroad, and only preliminary studies are carried out by the teacher W U Wutong from China Pharmaceutical University in China (Preliminary Study on the Modification of Pancreatic Kallikrein with PEG 5000, Pharmaceutical Biotechnology, 2006 (13): 409-412). The kininogenase is randomly modified at amino groups with PEG having a molecular weight of 5000 Dalton and having succinimide carbonate as a reactive group. The resulting product has a poor uniformity and a less high stability, and is extremely susceptible to hydrolysis, and neither the half-life nor the immunogenicity is ameliorated significantly. Therefore, in order to develop a long-acting PEGylated kininogenase with a low immunogenicity and a high biological activity, it is necessary to select a more suitable modification method and PEG material.

SUMMARY OF THE INVENTION

Technical Problems to be Solved the present invention provides a PEGylated tissue kallikrein (KLK1) having a high biological activity, a long half-life, and a low immunogenicity, and use thereof in the preparation of drugs for treating mild to moderate acute thrombotic cerebral infarction.

A first objective of the present invention is to provide a PEGylated KLK1.

A second objective of the present invention is to provide a method for preparing the PEGylated KLK1.

A third objective of the present invention is to provide new use of the PEGylated KLK1 in the preparation of drugs for treating mild or moderate acute thrombotic cerebral infarction or diabetic nephropathy.

A fourth objective of the present invention is to provide a pharmaceutical composition comprising the PEGylated KLK1 and a pharmaceutically acceptable adjuvant.

A fifth objective of the present invention is to provide a pharmaceutically acceptable salt or a complex of a PEGylated KLK1 or a pharmaceutical composition thereof.

Technical Solutions

A PEGylated tissue kallikrein is provided, where the PEG has a molecular weight of 20 to 40 kDa, and is conjugated to the N-terminal primary amino of the tissue kallikrein.

The PEG is conjugated to the N-terminal primary amino of the tissue kallikrein through a propionaldehyde group.

The PEG molecule is linear or branched.

The PEG molecule is a branched PEG derivative, where the active group is propionaldehyde, butyraldehyde, acetaldehyde or valeraldehyde.

The PEGylated tissue kallikrein has a general structural formula shown as below:

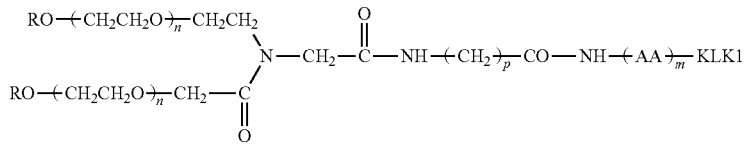

where R is H or C1-C4 alkyl; n is an integer from 10 to 1150, p is an integer from 1 to 3; AA is an N-terminal L-amino acid residue, and m is an integer from 0 to 5.

The alkyl is methyl, n is an integer between 57 and 455, p is 2, m is 0, and the KLK1 has a sequence as shown in SEQ ID No. 1 or SEQ ID No. 2.

n is an integer between 227 and 455.

A method for preparing a PEGylated tissue kallikrein includes: step 1: formulating a 0.1-30 mg/mL tissue kallikrein solution with a 10-50 mM sodium acetate buffer pH 4-6; step 2: reacting for 0.1 to 24 h at 4 to 37° C. at a molar ratio of tissue kallikrein:PEG:reductant=1:2-25:20-1000; and step 3: purifying by chromatography after reaction, to finally obtain a mono-PEGylated tissue kallikrein.

The reductant is preferably sodium cyanoborohydride.

Use of the PEGylated tissue kallikrein in the preparation of drugs for treating cerebral apoplexy is provided.

Use of the PEGylated tissue kallikrein in the preparation of drugs for treating diabetes mellitus induced nephropathy is provided.

A drug for treating cerebral apoplexy or diabetes mellitus induced nephropathy is provided, which comprises the PEGylated tissue kallikrein, a pharmaceutically acceptable salt or a complex thereof as the active ingredient.

The pharmaceutically acceptable salt is nontoxic when presents in the administered amount and concentration. Such salts are prepared to promote the administration of the drugs by altering the physical properties of the compound without affecting the exertion of the physiological effect. The useful changes in physical properties include reduction of the melting point to promote the transmucosal administration and increase of the solubility to facilitate the administration of a higher concentration of drugs.

The pharmaceutically acceptable salts include acid addition salts, for example, sulphate, hydrochloride, fumarate, maleate, phosphate, acetate, citrate, lactate, tartrate, methanesulfonate, and benzene sulfonate, etc. The pharmaceutically acceptable salts may be derived from acids, including hydrochloric acid, maleic acid, sulfuric acid, phosphoric acid, acetic acid, citric acid, lactic acid, and tartaric acid, etc.

A Pharmaceutically acceptable carrier and/or excipient may be blended into the pharmaceutical composition according to the present invention to facilitate the administration of a specific kallikrein. Carriers suitable for the implementation of the present invention include calcium carbonate, calcium phosphate, various sugars (lactose, glucose, sucrose) or various starches, cellulose derivatives, gelatin, vegetable oil, PEG, and physiologically compatible solvents, (including sterile water solutions, salt solutions and dextrose for injection).

Beneficial Effects

In addition to the advantages of significantly extended half-life, significantly reduced immunogenicity and stable and uniform structure, the biological activity of the PEGylated KLK1 provided in the present invention is improved to a higher extent.

As can be seen from the results of analysis by high performance gel filtration, the conjugate prepared has no considerable impurities, and the purities are all higher than 98%, thus meeting the standards in Chinese Pharmacopoeia.

Figure 2:
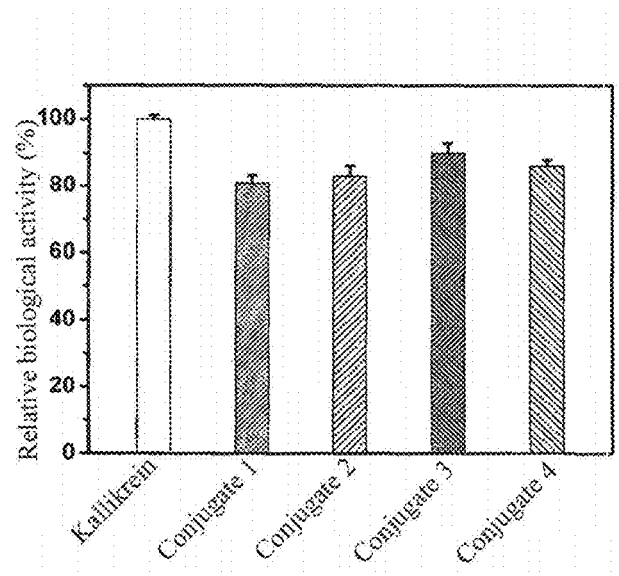

FIG. 2 shows in vitro biological activity of different PEG-KLK1 conjugates.

As can be known from the in vitro activity detection results, the conjugates 1 to 4 retain 81%, 83%, 90%, and 86% of the activity of the original protein respectively, and thus it can be seen that among the PEGylated products, the conjugate 3 has the best biological activity, and the conjugate 1 has the worst activity.

Figure 3:
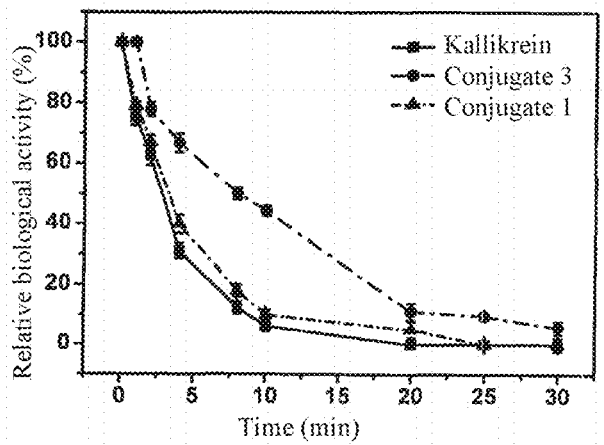

FIG. 3 shows the thermostability of different PEG-KLK1 conjugates.

It can be known that the activity of the unmodified kallikrein is substantially lost after standing for 10 min at 65° C., and the conjugates 1 and 3 both have increased thermostability at a high temperature, where the conjugate 3 still has a certain activity-after standing for 20 min at 65° C., indicating that the kallikrein has increased thermostability after PEG modification, and the thermostability of the conjugate 3 is significantly better than that of the conjugate 1.

Figure 4A:
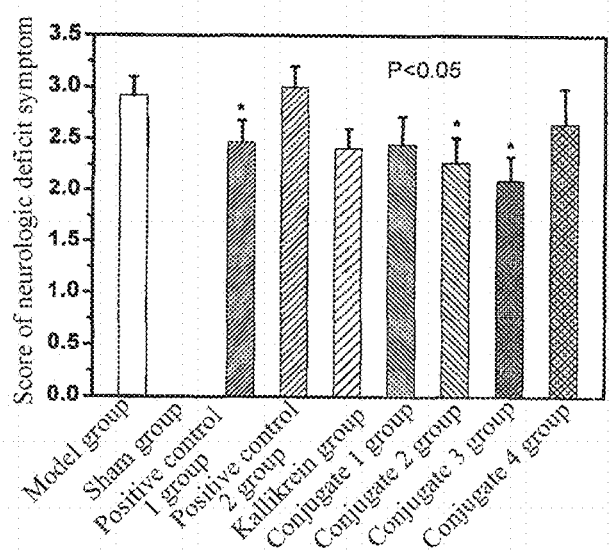

FIG. 4a shows scores of neurologic deficit symptoms in experimental animals from different groups. It can be known from the experimental results that the positive control 1 group (urinary kallikrein), conjugate 2 group and conjugate 3 group all have significant differences from the model group, and the experimental animals in the conjugate 2 and 3 groups after administration have scores of neurologic deficit symptoms that are apparently higher than that of the positive control 1 group.

Figure 4B:
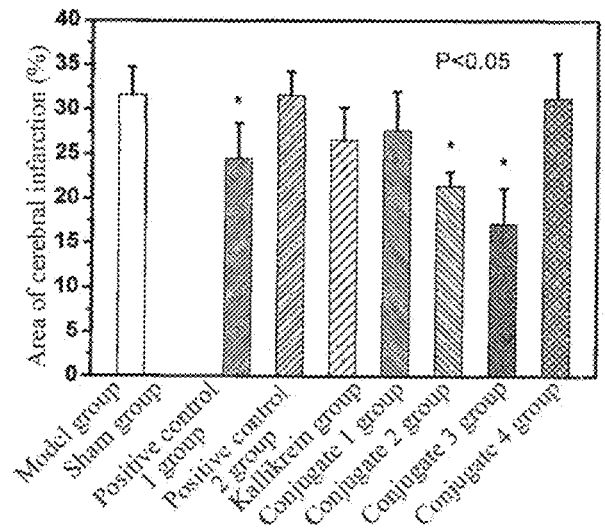

FIG. 4b shows areas of cerebral infarction in experimental animals from different groups. It can be known from the experimental results that the positive control 1 group (urinary kallikrein), the conjugate 2 group and the conjugate 3 group all have significant differences from the model group and the experimental animals in the conjugate 2 and 3 groups after administration have an area of cerebral infarction that is lower than that of the positive control 1 group. It can be seen that all of the conjugate 4, the positive control 2 (tPA) and kallikrein have no apparent amelioration on the cerebral infarction status of the model animals; the conjugate 1 can slightly ameliorate the cerebral infarction status of the experimental animals; and the conjugates 2 and 3 have a better therapeutic effect on acute thrombotic cerebral infarction as compared with the positive control 1 (urinary kallikrein), the positive control 2 (tPA) and kallikrein.

FIGS. 4a and 4b compare the efficacy of different PEG-KLK1 conjugates in the treatment of cerebral apoplexy.

Figure 5A:
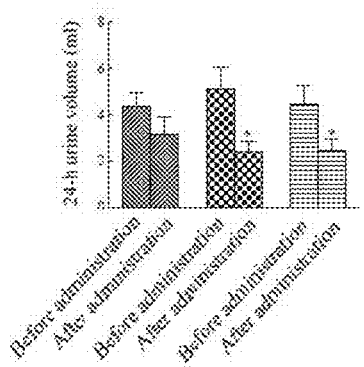

FIG. 5a shows variations in the urine volume of the experimental animals before and after administration. It can be known from the results that the original protein group and the conjugate 3 group have significantly reduced 24-h urine volume after administration as compared with the model group.

Figure 5B:
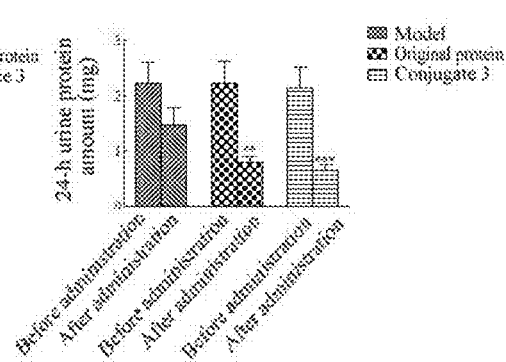

FIG. 5b shows variations in 24-h urine protein amount of the experimental animals before and after administration. It can be known from the results that, the original protein group and the conjugate 3 group have significantly reduced 24-h urine protein after administration, as compared with the model group, and the reduction in the conjugate 3 group is more significant.

Figure 5C:
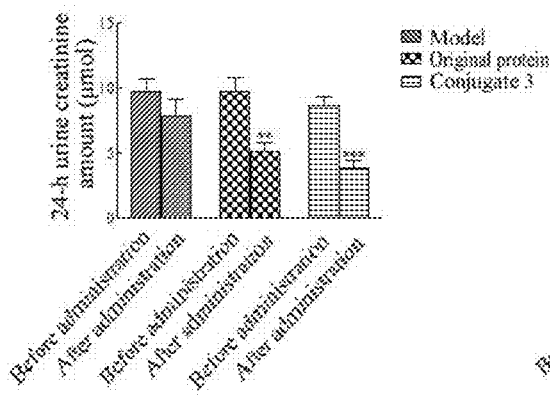

FIG. 5c shows variations in 24-h urine creatinine amount of the experimental animals before and after administration. It can be known from the results that the original protein group and the conjugate 3 group have significantly reduced 24-h urine creatinine after administration, as compared with the model group, and the reduction in the conjugate 3 group is more significant.

Figure 5D:
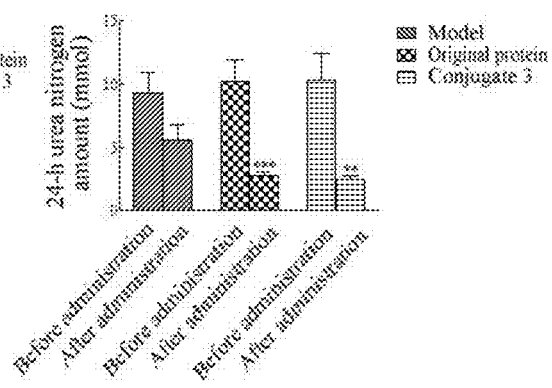

FIG. 5d shows variations in 24-h urea nitrogen amount of the experimental animals before and after administration. It can be known from the results that the original protein group and the conjugate 3 group have significantly reduced 24-h urea nitrogen after administration, as compared with the model group, and the reduction in the conjugate 3 group is more significant. It can be seen that, both the kallikreinogen protein and PEG modified kallikrein conjugate can effectively ameliorate the renal injury caused by diabetic nephropathy of experimental animals. Also, it can be known from the fact that the dosing interval of the Pegylated kallikrein is 1-fold longer than that of the kallikreinogen protein that, the half-life in vivo of kallikrein after PEG modification is apparently extended, and the efficacy is significantly improved.

FIGS. 5a to 5d show the therapeutic effect of the PEG-KLK1 conjugate on diabetic nephropathy.

Figure 6:
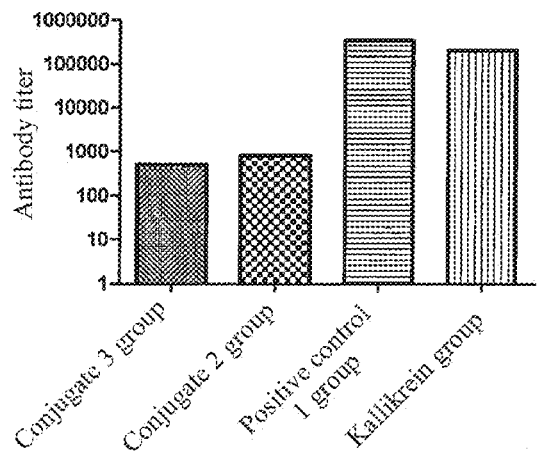

FIG. 6 shows immunogenicity of different PEG-KLK1 conjugates.

Experimental results show that after various PEG-KLK1 conjugates are injected into the mice, the antibody titers generated in experimental animals of the conjugate groups 2 and 3 are far lower than those in the experimental animals of the positive control 1 group (urinary kallikrein) and the non-PEGylated kallikrein group, indicating that the PEGylated conjugates 2 and 3 have a immunogenicity that is far lower than that of the positive control 1 (urinary kallikrein) and non-PEGylated kallikrein, and the conjugate 3 has a relatively slightly lower immunogenicity for mice than the conjugate 2.

Figure 7:
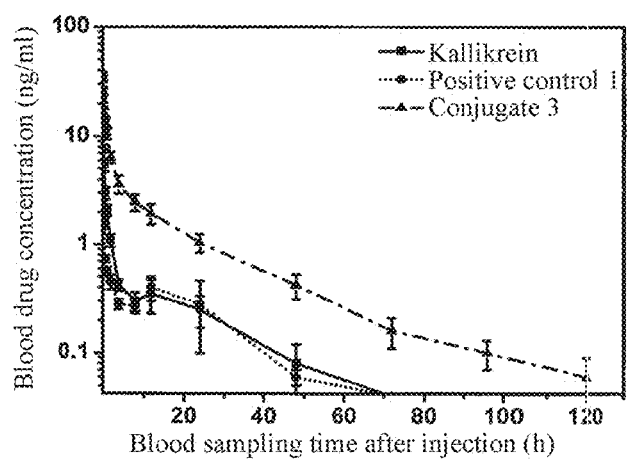

FIG. 7 shows variations in blood drug concentration in rats after intravenous administration with various PEG-KLK1 conjugates.

Pharmacokinetics of various PEG-KLK1 conjugates is detected by isotopic tracing. Experimental results show that the reduction in the blood drug concentration of the conjugate 3 is slow, the half-life is obviously extended, the AUC is greatly increased, and plasma clearance rate is considerably decreased, as compared with the positive control 1 group (urinary kallikrein) and kallikrein.

Figure 8A:
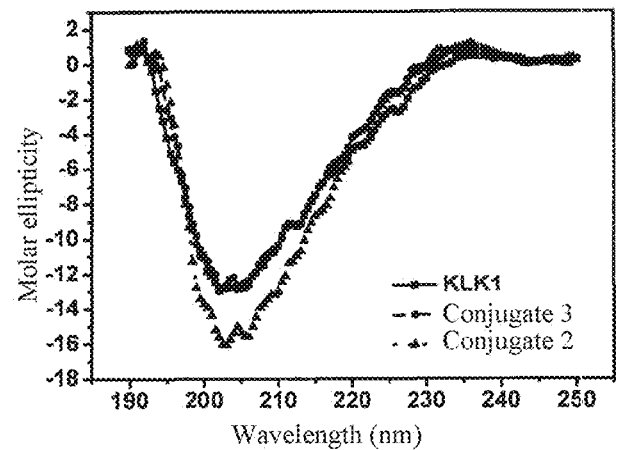

FIG. 8a compares far ultraviolet circular dichroism spectra of various PEG-KLK1 conjugates and the original protein.

Figure 8B:
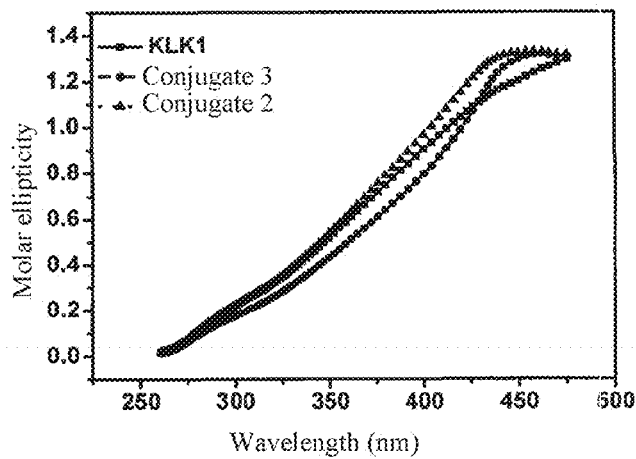

FIG. 8b compares near ultraviolet circular dichroism spectra of various PEG-KLK1 conjugates and the original protein.

FIGS. 8b and 8b compares circular dichroism spectra of various PEG-KLK1 conjugates and the original protein. As can be seen from the circular dichroism spectra, KLK1 has essentially no change in the near and far ultraviolet circular dichroism spectra after PEG modification, indicating that no change occurs to the secondary and tertiary structure of the modified KLK1.

Figure 9:
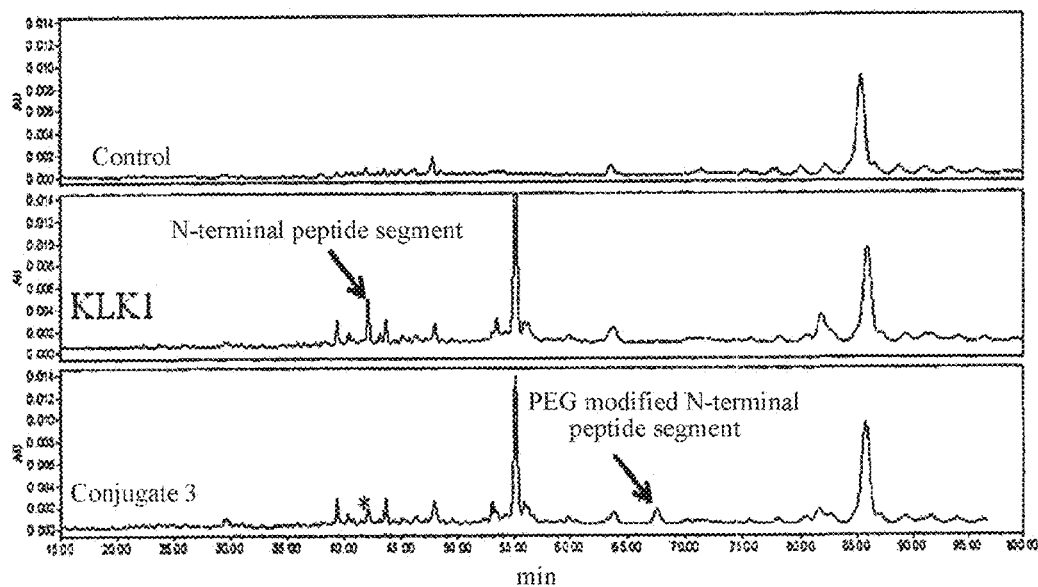

FIG. 9 compares peptide mapping by enzymolysis of the conjugate 3 and the original protein.

As can be seen from the peptide mapping by enzymolysis of the conjugate 3 and the original protein, the conjugate 3 is modified by PEG at the N terminus of the protein.

Figure 10:
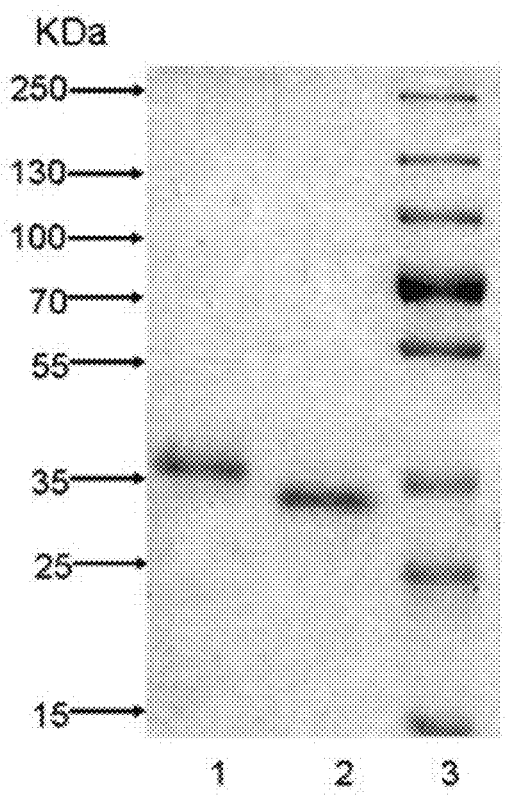

FIG. 10 identifies the expression of a recombinant hK1 protein in *Pichia pastoris* X-33 engineered bacterium.

In FIG. 10, lane 1 is a recombinant hK1 protein with a greater relative molecular weight, lane 2 is a recombinant hK1 protein with a lower relative molecular weight, and lane 3 is a prestained protein loading Marker with a molecular weight ranging from 10 to 250 KD. The physicochemical properties and biological activity of the two recombinant hK1 proteins with different molecular weights have no difference, except that the glycosylation modifications are different.

Figure 11:
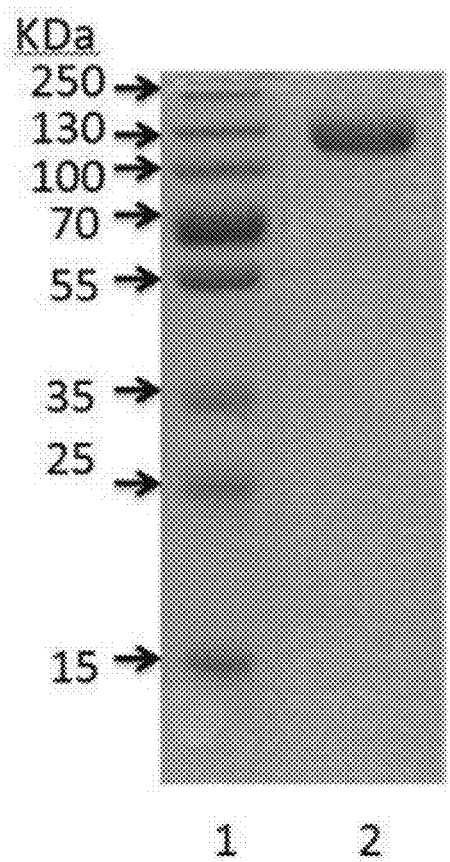

FIG. 11 shows protein electrophoretic analysis of PEGylated recombinant human kallikrein expressed in yeasts.

In FIG. 11, lane 1 is a prestained protein loading Marker with a molecular weight ranging from 10 to 250 KD, and lane 2 is a recombinant hK1 protein modified with Y-PALD-30K. As can be seen from the results of protein electrophoresis, the conjugate prepared has no apparent impurities, and has significantly increased molecular weight and higher purity as compared with the original protein.

Figure 12:
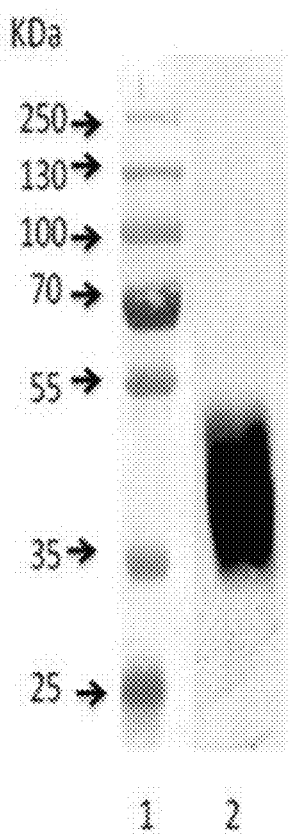

FIG. 12 shows immunoblot of a culture supernatant of a recombinant hK1 protein stably expressed in CHO-S cell line.

In FIG. 12, Lane 1 is a prestained protein loading Marker with a molecular weight ranging from 10 to 250 KD, and lane 2 is the culture supernatant on day 13 of CHO-S host cells producing the recombinant hK1 protein.

Figure 13:
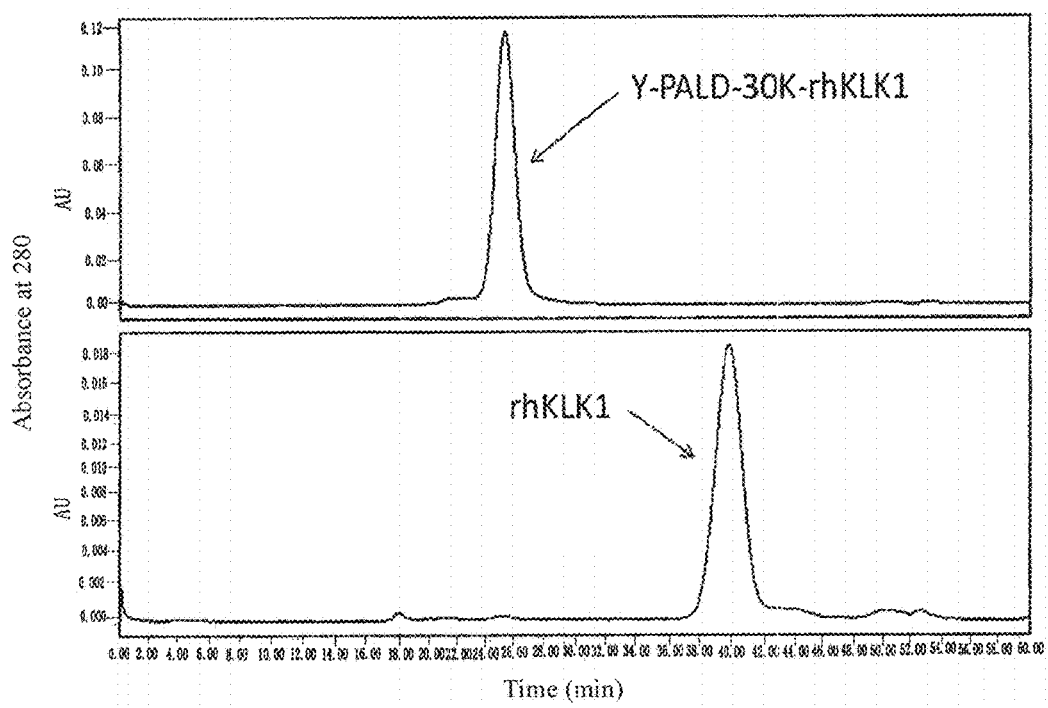

FIG. 13 shows analysis by HPLC of PEGylated recombinant human kallikrein expressed in CHO cells.

The purity of the prepared PEGylated products is analyzed by HPLC. As can be seen from the results from HPLC analysis, the conjugate prepared has a high purity of up to more than 98%.

DETAILED DESCRIPTION OF THE INVENTION

Definitions

The following abbreviations are used herein:
PEG: polyethylene glycol;
Y-PALD-20K: branched PEG propionaldehyde comprising two straight chains of methoxy polyethylene glycol, with a molecular weight of 20 KDa, and a Y-shaped structure;
Y-PALD-30K: branched PEG propionaldehyde comprising two straight chains of methoxy polyethylene glycol, with a molecular weight of 30 KDa, and a Y-shaped structure;
Y-PALD-40K: branched PEG propionaldehyde comprising two straight chains of methoxy polyethylene glycols, with a molecular weight of 40 KDa, and a Y-shaped structure;
KLK1: tissue kallikrein extracted from porcine pancreas, and kallikrein extracted from human urine.
hK1: recombinant human kallikrein.
mPEG-SC5000: linear monomethoxy PEG, with a molecular weight of 5000, and an active group of succinimide carbonate.

The term "conjugate" as used herein refers to a mono-PEGylated product of KLK1.

Several mono-PEGylated products of KLK1 referred to as "SC-PEG5000-KLK1, Y-PALD-20K-KLK1, Y-PALD-30K-KLK1, Y-PALD-40K-KLK1" herein may be collectively referred to as PEG-KLK1 or the conjugate.

"Polyethylene glycol" is a polymer of ethylene oxide and water, which may be branched or linear. "Polyethylene glycol" or "PEG" plus a figure suffix denotes its average molecular weight. For example, PEG-20000 refers to polyethylene glycol with a molecular weight of around 20000; alternatively, "PEG" may be omitted, for example, Y-PALD-20K denotes Y-shaped PEG propionaldehyde with a molecular weight of around 20000, and a structural formula shown as below:

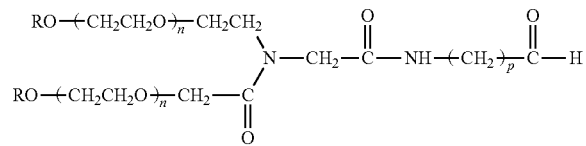

In the formula, R is H or C1-C4 alkyl, and preferably methyl; n is an integer from 10 to 1000, preferably an integer between 57 and 455, and more preferably an integer between 227 and 455; and p is an integer from 1 to 3, and preferably 2. Polyethylene glycol has advantageously a molecular weight ranging from about 20000 Da to about 40000 Da. More particularly, polyethylene glycol has a molecular weight selected from the group consisting of: 20000 Da, 30000 Da, and 40000 Da. In a particular embodiment, the molecular weight of polyethylene glycol is 30000 Da.

In the present invention, KLK1 may be derived, cloned or generated, from any sources, including animals, or by recombinant DNA technologies or a combination thereof. For example, KLK1 may be extracted from animal tissues or urine, including, but not limited to, porcine pancreas, and human urine. In a particular embodiment of the conjugate according to the present invention, KLK1 has at least about 60% sequence identity to the protein comprising the sequence of SEQ ID NO: 1 or SEQ ID NO: 2.

In a particular embodiment, the protein is a tissue-type KLK1 derived from porcine pancreas, which has a sequence as shown in SEQ ID NO: 1. In another embodiment, KLK1 is derived from recombinant humanized KLK1, which has a sequence as shown in SEQ ID NO: 2.

Fragments of the protein shown in SEQ ID NO: 1 or SEQ ID NO: 2 are also encompassed in the definition of the protein used in the conjugate according to the present invention. The "fragments of the protein shown in SEQ ID NO: 1 or SEQ ID NO: 2" means that the polypeptide sequence may include less amino acids than SEQ ID NO: 1 or SEQ ID NO: 2, but still includes adequate amino acids to impart activity of catalyzing the release of biological active peptide from the macromolecular precursor (kininogen).

It is well known in the art that the polypeptide may be modified by substituting, inserting, deleting and/or adding one or more amino acids while the enzymatic activity is maintained. For example, it is common to substitute one amino acid at a given position with a chemically equivalent, amino acid without affecting the function and property of the protein. Therefore, it is anticipated that a functionally equivalent product may be produced by substituting one negatively charged residue with another or substituting one positively charged residue with another.

A linker for covalently binding PEG to KLK1 may be any biocompatible linker. "Biocompatible" denotes that the compound or group is nontoxic, and can be used in vitro or in vivo without causing injury, vomit, disease or death. PEG can be bound to a linker, for example, by an ester bond, a thiol bond or an amido bond.

In the present invention, the most preferred biocompatible linkers have a common characteristic that they are conjugated to an N-terminal amino of KLK1 through a propionaldehyde group. In addition, KLK1 may be conjugated directly to PEG through an amino, mercapto, hydroxy or carboxyl group. In a most preferred embodiment, PEG is conjugated to an N-terminal amino of KLK1 through an amido bond.

The method for preparing PEGylated KLK1 according to the present invention includes reacting a certain amount of PEG and a certain amount of KLK1 for a sufficient period of time in a buffer, to allow PEG to covalently bind to KLK1. In a particular embodiment, the KLK1 is derived from pancreas, and more particularly from porcine pancreas. More particularly, the KLK1 comprises a sequence of SEQ ID NO: 1. In an embodiment, the PEG is of Y-PALD type.

In a particular embodiment, the buffer has a pH value ranging from about 4.0 to about 9.0. The most preferred pH value ranges from about 5.0 to 6.0, e.g., about 5.0, 5.1, 5.2, 5.3, 5.4, 5.5, 5.6, 5.7, 5.8, 5.9 or 6.0.

In addition, PEGylation of kallikrein is carried out at a protein concentration of about 0.5 to 30 mg/mL, more particularly preferably about 2 to 20 mg/mL, most particularly preferably about 3 to 15 mg/mL. In a particular embodiment, the kallikrein PEGylated at these protein concentrations is derived from porcine pancreas, and more particularly, the kallikrein comprise a sequence of SEQ ID NO: 1 or SEQ ID NO: 2.

At an elevated protein concentration, the PEGylation reaction is carried out quickly, within less than 3 h. In addition, The molar ratio of the PEG to kallikrein is not more than 25:1. For example, the molar excess is less than 25:1, 20:1, 19:1, 18:1, 17:1, 16:1, 15:1, 14:1, 13:1, 12:1, 11:1, 10:1, 9:1, 8:1, 7.5:1, 7:1, 6.5:1, 6:1, and 5.5:1.

The present invention is further illustrated through the following examples. However, any example or combinations thereof should not be understood as limiting the scope or implementation of the present invention.

Example 1: Preparation and Analysis of PEG Conjugates of KLK1

Preparation Example 1: Preparation, Purification and Identification of the PEGylated KLK1 of the Present Invention 1. Preparation of PEG Conjugate Sample Kallikrein (available from Changzhou Qianhong BioPharmaceutical Co., Ltd.) was dissolved in a 50 mM acetic acid-sodium acetate buffer (pH 5.0) to formulate an 8 mg/mL solution, and reacted respectively with Y-PALD20K, Y-PALD30K, Y-PALD40K (purchased from Beijing Jiankai science and Technology Co. Ltd.) at a molar ratio of kallikrein:PEG:sodium cyanoborohydride of 1:10:100. After 12 h of the reaction at 4° C., 1 M glycine was added to terminate the reaction. 3 mono-modified products Y-PALD-20K-KLK1 (conjugate 2), Y-PALD-30K-KLK (conjugate 3), and Y-PALD-40K-KLK1 (conjugate 4) were prepared.

In addition, kallikrein was dissolved in a 50 mM Tris-HCl buffer (pH 8.5) to formulate an 8 mg/mL kallikrein solution, and reacted with mPEG-SC5000 (purchased from Beijing Jiankai science and Technology Co, Ltd.) at a molar ratio of kallikrein; PEG of 1:8. The reaction was carried out for 0.5 h at 4° C. A mono-modified product SC-PEG5000-KLK1 (conjugate 1) was prepared, for comparison with the modified product according to the present invention. The conjugates 1, 2, 3 and 4 had a yield of 40%, 55%, 58%, and 61% respectively.

2. Purification of PEG Conjugate Sample 2.1 Removal of Unreacted PEG by Chromatography Chromatography conditions: Q ion exchange column (purchased from GE Inc., HiTrap Q HP 5 mL), solution A: 20 mM Tris-HCl (pH 8.0), solution B: 1 M NaCl in 20 mM Tris-HCl (pH 8.0), flow rate 2.5 mL/min, and detection wavelength 280 nm.

Sample Loading: The modified product was adjusted to pH 8.0 with a 0.5 M NaOH solution, and bound to the Q ion exchange column.

Equilibrium: The column was washed with 5 column volumes of the solution A.

Collection: The modified product was eluted off with 50% (v/v) of the solution B, and the sample corresponding to the elution peak was collected.

2.2 Purification of Mono-Modified PEG Conjugates by Chromatography

Chromatography conditions: Hiload 16/60 Superdex 200 pg (purchased from GE Inc.) semi-preparative gel filtration column, eluant: PBS, flow rate 1.5 mL/min, and detection wavelength 280 nm.

3. Detection of PEG Conjugate Sample

Chromatography conditions: HPLC (Waters, e2695 HPLC), Superdex 200 10/300 GL (purchased from GE Inc.), mobile phase: 0.1 M $Na_2SO_4$ in PBS (pH 7.4), flow rate 0.4 mL/min, detection wavelength 280 nm, sampling volume 50 µL, and detection time 60 min.

Figure 1:
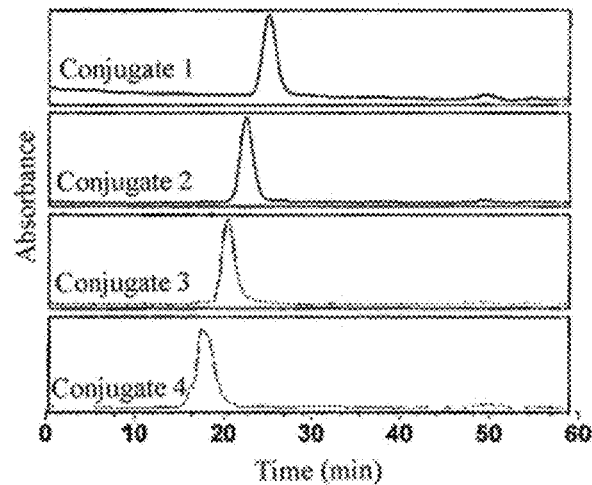
FIG. 1 shows purity analysis of different PEG-KLK1 conjugates by HPLC-SEC.

Analysis results are shown in FIG. 1. As can be seen from FIG. 1, the 4 mono-modified products SC-PEG5000-KLK1 (conjugate 1), Y-PALD-20K-KLK1 (conjugate 2), Y-PALD-30K-KLK1 (conjugate 3), and Y-PALD-40K-KLK1 (conjugate 4) prepared all have a purity that is higher than 98%, and the molecular weight of the conjugates 1 to 4 gradually increases with the gradual increase of the molecular weight of PEG employed.

The methods in Preparation Examples 2 to 4 was the same as that in Preparation Example 1 except for the pH value, reaction temperature, reaction time, protein concentration, and molar ratio. The specific parameters and yields are shown in a table below:

|  | Preparation Example 2 | Preparation Example 3 | Preparation Example 4 |
| --- | --- | --- | --- |
| pH | 5.0 | 5.5 | 6.0 |
| Modifier | Y-PALD-30K | Y-PALD-30K | Y-PALD-30K |
| Molar ratio (protein:PEG:reductant) | 1:5:100 | 1:15:15000 | 1:25:2500 |
| Reaction temperature | 4° C. | 25° C. | 37° C. |
| Reaction time (h) | 24 | 10 | 0.5 |
| Protein concentration (mg/mL) | 15 | 10 | 0.5 |
| Yield (%) | 61 | 59 | 63 |

The activity and purity of the mono-modified products prepared in Preparation Examples 2, 3, and 4 have no significant difference from those of the mono-modified product conjugate 3 obtained in Preparation Example 1. The PEG-KLK1 conjugates employed in the following examples are all the conjugates obtained in Preparation Example 1.

Example 2: Detection of In Vitro Activity of PEG-KLK1 Conjugates

N-benzoyl-L arginine ethyl ester hydrochloride (BAEE, purchased from sigma Inc.) may be degraded by Kallikrein, and the activity of kininogenase may be determined according to the change in the absorbance before and after the enzymatic reaction, see *Pharmacopoeia of People's Republic of China*, pages 850-851, Section 2, 2010 version for a particular determination method. Samples to be detected were, respectively, SC-PEG5000-KLK1 (conjugate 1), Y-PALD-20K-KLK1 (conjugate 2), Y-PALD-30K-KLK1 (conjugate 3), and Y-PALD-40K-KLK1 (conjugate 4) from Preparation Example 1, and the original unmodified protein. The comparison results of relative activity thereof are shown in FIG. 2.

As can be seen from the results in FIG. 2, the activity of the original protein is reduced to some degree after PEG modification. As compared with the original unmodified protein, the conjugates 1 to 4 retain 81%, 83%, 90%, and 86% of the activity of the original protein respectively. Among the PEG modified products, the conjugate 3 has the highest biological activity, and the conjugate 1 has the lowest activity. It can be seen that the PEG modified KLK1 according to the present invention retains the in vitro biological activity of the original protein to a greater degree. The conjugate 1 has an activity consistent with that reported in literatures.

Secondly, according to a general rule of PEG modification, the influence on the activity is increased with increasing molecular weight of the PEG employed. However, this rule is not demonstrated in the present invention. The PEG modifiers employed herein all have a molecular weight that is far greater than 5000 Da, but the biological activity of the modified kallikrein is still greater than the former modified with PEG5000, and the conjugate 3 with PEG having a molecular weight of 30 KDa has the highest biological activity.

Example 3: Thermostability of PEG-KLK1 Conjugates

In order to confirm whether the PEG modification can increase the stability of kallikrein, the activity of the conjugates 1 and 3 and the original protein after standing for a period of time in a water bath at 65° C. was detected respectively in this example. The method specifically included the following steps. The conjugates 1 and 3 and the unmodified kallikrein dissolved in a PBS buffer at a protein concentration of 1 mg/mL were stood in a water bath at 65° C., sampled at 0 min, 2.5 min, 5 min, 7.5 min, 10 min, 20 min, 25 min, and 30 min respectively, and stored in freezer at 4° C. for later use. After sampling, the biological activity was detected by employing the method (i.e., the method described in appendix IX F in *Pharmacopoeia of People's Republic of China*, Section 3, 2005 version). The detection results are shown in FIG. 3.

As can be seen from FIG. 3, in comparison with the original protein, the thermostability of the PEG modified kallikrein is increased; however, the increase in the thermostability of the conjugate 1 is unobvious, and the thermostability of the conjugate 3 is significantly increased as compared with the original protein.

Example 4: Comparison of Efficacy of Various PEG-KLK1 Conjugates in Treatment of Cerebral Apoplexy A cerebral ischemia reperfusion model of middle cerebral artery obstruction (MCAO) was established by thread embolizing the internal carotid artery of SD rats (purchased from Shanghai Sippr bk Laboratory Animal Co. LTD.) A positive control 1 group (urinary kallikrein, Guangdong Tianpu Biochemical Pharmaceutical Co., LTD.), a positive control 2 group (tPA, Shanghai Boehringer Ingelheim Pharmaceuticals Co., LTD), a model control group (PBS), a sham group, a kallikrein group (from Changzhou Qianhong Biochemical Pharmaceutical Co., LTD.), a conjugate 1 group, a conjugate 2 group, a conjugate 3 group, and a conjugate 4 group were arranged respectively. Administration by injection through vena caudalis was performed once at 3 μg/kg (calculated according to the protein amount) immediately after the cerebral ischemia reperfusion. Neurologic deficit symptoms were observed 24 h after the reperfusion, and the cerebral infarction area was determined.

In the model group, an equal volume of PBS was injected through vena caudalis into the rat. In the sham group, only blood vessels were separated, no embolizing thread was inserted, and an equal volume of PBS was injected through vena caudalis into the rats.

Neurologic deficit symptoms were evaluated employing an improved Bederson 5-point system method. Neurologic deficit symptoms of the rats after brain trauma were evaluated by a single-blind method, i.e., the animals were marked according to groups by designers of the experiment, and scores of the neurologic deficit symptoms were given by experimenters blind to the grouping situation.

The cerebral infarction area was calculated employing the following method. Cerebrums of the SD rats were stained with TTC (2,3,5-triphenyltetrazolium chloride) and then the photographs were subjected to statistics using an image analysis software, and the percentage of cerebral infarction area was calculated according to the following formula:

% cerebral infarction area=100×(total ischemic area/ total area on the right side)

Experimental results are as shown in FIG. 4 and Tables 1 and 2.

TABLE 1

Efficacy studies on PEG-KLK1 conjugates, kallikrein and positive control drugs-comparison of neurologic deficit symptoms

| Groups | Total number of animals (n) | Failed in operation (n) | Death (n) | Sample (n) | Score of neurologic deficit symptom |
|---|---|---|---|---|---|
| Model group | 25 | 3 | 2 | 20 | 2.92 ± 0.18 |
| Sham group | 15 | 0 | 0 | 15 | 0.00 ± 0.00 |
| Positive control 1 group | 26 | 2 | 3 | 21 | 2.47 ± 0.21* |
| Positive control 2 group | 24 | 2 | 0 | 22 | 3.00 ± 0.20 |
| Kallikrein group | 25 | 2 | 1 | 22 | 2.41 ± 0.19 |
| Conjugate 1 group | 25 | 2 | 1 | 22 | 2.45 ± 0.27 |
| Conjugate 2 group | 25 | 2 | 0 | 23 | 2.27 ± 0.24* |
| Conjugate 3 group | 23 | 1 | 2 | 20 | 2.10 ± 0.23* |
| Conjugate 4 group | 26 | 2 | 3 | 21 | 2.65 ± 0.34 |

TABLE 2

Efficacy studies on PEG-KLK1 conjugates, kallikrein and positive control drugs-comparison of cerebral infarction areas

| Groups | Total number of animals (n) | Failed in operation (n) | Death (n) | Sample (n) | Cerebral infarction area (%) |
|---|---|---|---|---|---|
| Model group | 25 | 3 | 2 | 20 | 31.62 ± 3.10 |
| Sham group | 15 | 0 | 0 | 15 | 0.00 ± 0.00 |
| Positive control 1 group | 26 | 2 | 3 | 21 | 24.49 ± 3.96* |
| Positive control 2 group | 24 | 2 | 0 | 22 | 31.55 ± 2.71 |
| Kallikrein group | 25 | 2 | 1 | 22 | 26.52 ± 3.67 |
| Conjugate 1 group | 25 | 2 | 1 | 22 | 27.67 ± 4.34 |
| Conjugate 2 group | 25 | 2 | 0 | 23 | 21.34 ± 1.70* |
| Conjugate 3 group | 23 | 1 | 2 | 20 | 17.16 ± 4.07* |
| Conjugate 4 group | 26 | 2 | 3 | 21 | 31.27 ± 5.08 |

Experimental results indicate that in experiments where neurologic deficit symptoms are scored and cerebral infarction area is calculated, neither of the conjugate 4 group, positive control 2 (tPA) and kallikrein has apparently ameliorated cerebral infarction states in the model animals, whereas the positive control 1 group (urinary kallikrein), conjugate 1 group, conjugate 2 group, and conjugate 3 group all have significant differences from the model group, and both the conjugate 2 group and conjugate 3 group have higher therapeutic effects against acute atherothrombotic cerebral infarction, than that of the positive control 1 group. In summary, in comparison with the original protein unmodified with PEG and two positive drugs, conjugates 2 and 3 had apparent protective effects against cerebral ischemic injury in cerebral ischemia reperfusion model of SD rats established employing the MACO method, and had efficacy superior to that of commercially available products. The conjugate 1 only partially ameliorated the cerebral infarction state in the model animals, whereas the conjugate 4 essentially did not reduce the cerebral infarction area in the experimental animals, and did not ameliorate the neurologic deficit symptoms, indicating that the two conjugates failed to play a role in the treatment of cerebral infarction diseases, and failed to ameliorate the final physiological state of patients with cerebral infarction. Thus it can be seen that, the employment of PEG modification to ameliorate pharmacological efficacy or pharmacokinetic properties of protein polypeptides has higher differences across different conjugates.

Example 5: Comparison of Efficacy of PEG-KLK1 Conjugates and the Original Protein in the Treatment of Nephropathy Caused by Diabetes Mellitus db/db mice (purchased from Shanghai Slaccas Experimental Animal Co., LTD., grade SPF, 8-week aged, male, with a conformity certification No. of 2007000552656) were employed as animal models for diabetic nephropathy. A model group, a kallikrein (purchased from Changzhou Qianhong Biochemical Pharmaceutical Co., LTD.) original protein group and a conjugate 3 group were provided respectively. The administered dose was 2 µg/kg (calculated according to the protein amount), through vena caudalis, where the model group and the original protein group were dosed once a week, and the conjugate 3 group was dosed once every 2 weeks, for 2 continuous months before detection of urine volume, urine protein, urea nitrogen and urine creatinine. (Urine protein detection kits, urine creatinine detection kits, and urea nitrogen detection kits were all purchased from Nanjing Jiaticheng Bioengineering Co., LTD.)

Detection results are seen in FIG. 5. As can be seen from the experimental results that, in comparison with the model group, the experimental animals in the original protein group and the conjugate 3 group had significantly decreased numerical values of urine volume, urine protein, urine creatinine and urea nitrogen, indicating that kallikrein has an apparent therapeutic effect in the treatment of nephropathy caused by diabetes mellitus. In addition, the conjugate 3 group had more apparent reduction in urine protein, urine creatinine and urea nitrogen in comparison with the original protein group. If can be known from the experimental arrangement that, the conjugate 3 group was dosed once every 2 weeks, and the original protein group was dosed once every 1 week. Through comprehensive analysis, the conjugate 3 group received efficacy apparently superior to that of the original protein group, indicating that kallikrein has apparently extended half-life in vivo after PEG modification, thus significantly improve the efficacy.

Example 6: Immunogenicity of PEG-KLK1 Conjugates

Relative immunogenicity of different PEG-KLK1 conjugates to mice was determined in this example, and compared with the original protein. The experiment was divided into a conjugate 2 group, a conjugate 3 group, a urinary kallikrein group and an original protein group. 1 mg/kg (calculated according to the protein amount) of the above protein was injected through vena caudalis into the mice at a frequency of twice a week, for 4 continuous weeks. Blood was taken from eye sockets 1 week after administration. The anti-kallikrein antibody level in serum was determined by indirect. ELISA, with results shown in FIG. 6.

As can be found from the results that conjugates 2 and 3 have antibody titers on mice that are much lower than those of kallikrein from porcine pancreas and urinary kallikrein sourced from human urine, indicating that the PEG modification can apparently reduce the protein immunogenicity, and the conjugate 3 has slightly lower relative immunogenicity to mice than the conjugate 2.

Example 7: Pharmacokinetic Studies on PEG-KLK1 Conjugates

The in vivo blood drug concentrations of kallikrein before and after the PEG modification were studied employing a $^{125}I$ isotope labelling tracer method in this example. In order to reduce the absorption of the labelled drug by the thyroid gland of rats, 1 ml of a 1% KI (Sinopharm Group) solution was intraperitoneally injected about 8 hours before the experiment, to saturate the thyroid gland of the rats. The rats were randomly divided into 3 groups, i.e., a conjugate 3 group, a kallikrein group, and a urinary kallikrein group, 8 in each group, half male and half female (purchased from Experimental Animal Center of Zhejiang Province).

A particular operation method is as follows:

1. Hydroxy on the amino acid residue phenyl ring in a protein molecule is substituted with radioiodine, to obtain the above protein with $^{125}I$ having a radioactive tracing effect.

2. Numbering is performed on the rats using picric acid according to the numbering rule, and weighing is performed. After fixing with a rat fixer, administration is performed by injection through vena caudalis (1.5 U/kg). The rat is let go immediately after the dosage, and allowed to move around, drink water, and eat food freely.

3. 0.2 mL of blood is taken from eye sockets 1 min, 3 min, 10 min, 20 min, 40 min, 60 min, 2 h, 4 h, 8 h, 12 h, 24 h, 48 h, 72 h, 96 h, and 120 h respectively after the dosage, and EDTA is added therein for anticoagulation.

4. The rat plasma is subjected to centrifugal separation at 5000 rpm for 3 min, and determined for plasma radioactivity using a gamma counter (Anke Zhongjia, GC-911), for 1 min.

5. Plasma is recovered after radioactivity determination, and undegraded proteinogenous drugs are separated by HPLC (Shimadzu LC-20AT).

A time-concentration curve is shown in FIG. 6, and each parameter is calculated as shown in Table 3.

TABLE 3

Comparison of pharmacokinetic parameters of PEG-KLK1
conjugate 3, kallikrein, and urinary kallikrein

| Sample | T½β (h) | AUC (μg/L * h) | CL (L/h/kg) | V (L/kg) |
| --- | --- | --- | --- | --- |
| Kallikrein | 18.81 | 18.59 | 0.13 | 3.53 |
| Positive control 1 (urinary kallikrein) | 17.49 | 11.68 | 0.21 | 5.16 |
| Conjugate 3 | 20.03 | 113.62 | 0.02 | 0.64 |

Experimental results indicate that, the pharmacodynamic model of the above drug belongs to a 2-compartment model. The half-life of the conjugate 3 is apparently extended and the area under the time-concentration curve (AUC) of the conjugate 3 is increased significantly, as compared with those of the original protein and urinary kallikrein. Secondly, the clearance rate from blood of the conjugate 3 is also significantly lower than those of the original protein and the positive control, and among the 3 groups, the conjugate 3 has the minimal apparent distribution volume, indicating that the conjugate 3 is more concentrated in the plasma than the other two unmodified proteins. Thus it can be seen that, as compared with unmodified kallikrein and urinary kallikrein derived from human urine, the conjugate 3 obtained by modifying kallikrein with PEG has a significantly increased half-life, and an apparently reduced metabolism rate, effectively extending the efficacy duration of kallikrein.

Example 8: Analysis of PEG-KLK1 Conjugates and Original Protein by Circular Dichroism Spectra Secondary and tertiary structures of the modified and unmodified proteins can be characterized with a circular dichroism spectrometer. The protein concentration ranged from 0.1 to 0.2 mg/mL. The sample was loaded into a circular dichroism cuvette, and detected for its circular dichroism spectra within the extreme ultraviolet region (190 nm-250 nm) and the near ultraviolet region (253 nm-480 nm), at a scanning bandwidth of 1 nm and a scanning speed of 500 nm/min. A corresponding buffer was used as the background in each detection, and values from detection of three times were averaged. As can be seen from FIG. 8a, the circular dichroism spectra within the extreme ultraviolet region of conjugates 2 and 3 have hardly any peak shift in the conjugate spectra, as compared with the original protein, indicating that PEG modification has no influence on the secondary structure of KLK1. As can be seen from FIG. 8b, the circular dichroism spectra within the near ultraviolet region of conjugates 2 and 3 have hardly any peak shift in the conjugate spectra, as compared with the original protein, indicating that PEG modification has no influence on the tertiary structure of KLK1. On the whole, through conjugates prepared by different modifiers, high-level structures of KLK1 have essentially no change. Because the conjugate has no change in the structure thereof after PEG modification, it loses less activity than the original protein, which is also validated by the data in Example 2. This result is also in line with the general rule of PEG modification. Most protein drugs have no change in the high-level structures thereof after PEG modification.

Example 9: Identification of PEG Modification Site of Conjugate 3

In order to determine the PEG modification site of conjugate 3, the conjugate 3 was subjected to an enzymolysis experiment with tryptase, and compared with the finger print of the original protein. The PEG modification site can be determined by comparison of the difference in peptide segments of the original protein and the modified product. Particular experimental steps include: adding 100 μL 0.5 mg/mL sample into 0.9 μL 1 mg/mL trypsin solution, and carrying out the reaction for 5 h at 37° C. The reaction was terminated by adding therein 10% (v/v) TFA after the reaction. Products of the enzymolysis were analyzed using a C18 reversion phase chromatographic column (purchased from Waters Inc.), with liquid A: $H_2O+0.1$ wt % TFA and liquid B: acetonitrile+0.1% (v/v) TFA as mobile phases respectively, at a loading amount of 80 μl, and a flow rate of 0.5 mL/min, for running time of 120 min. Gradient elution condition: 0-100 min 5%-60% (v/v) B. Comparison results of peptide maps are shown in FIG. 9. As can be seen from the diagram that, as compared with the map of the original protein, the N-terminal peptide segment of conjugate 3 has disappeared, but a PEG modified N-terminal peak appears at 68 min, indicating that PEG actually conjugates onto the N-terminal amino acid of KLK1, which is consistent with the expected result.

Example 10: Preparation of Yeast-Expressed Recombinant Human Kallikrein (hK1)

(1) Gene Design

According to a sequence of GenBank accession number AAA59455, the gene was subjected to codon optimization, to obtain a recombinant hK1 gene according to the present invention, as shown in SEQ ID No: 3.

(2) Construction of Expression Plasmid of Recombinant hK1 Gene

1. The fragment synthesized from the optimized recombinant hK1 full gene was constructed into pUC57 plasmids (purchased from Nanjing Genscript Biotechnology Co., LTD.), to obtain a long-term storage plasmid, denoted as pUC57-opt-hK1 plasmid.

2. The pUC57-opt-hK1 plasmid was used as a template, and upstream and downstream primers were introduced respectively into Xho I and Not I restriction enzyme cutting sites. Conduct the PCR amplification. The primers employed had sequences as follows:

```
Upstream primer:
                                          SEQ ID NO: 5
P1: GCCGCTCGAGAAGAGAGAAGCAGAGGCTATCGTC;
and Downstream primer:
                                          SEQ ID NO: 6
P2: AAGGAAAAAAGCGGCCGCCTAACTATTTTCAGCGAT
```

The total reaction volume was 50 μL, where 2.5 μL each of the primers at a concentration of 10 μmol/L was added, and 1 μL dNTP at a concentration of 10 mmol/L was added, and DNA polymerase employed was Q5 super-fidelity DNA polymerase (M0491S, purchased from New England Biolabs Inc.), 2 U/μL. Reaction condition included 98° C. for 10 s, 55° C. for 30 s, and 72° C. for 30 s. After 25 cycles, the product was analyzed by 1.0% agarose gel electrophoresis, and the size of the product was consistent with the expected size (760 bp). The obtained gene product was purified by a DNA gel recovery kit. After the purification, with Xho I and Not I double enzyme digestion, it was linked to pPICZα A (V19520, purchased from Invitrogen) by T4 ligase, transformed into DH5α competent cells, and cultured overnight at 37° C. in an LB flat plate containing Zeocin. The next day, positive clone bacteria were screened, sequenced, and aligned, to be completely identical with the expected sequence, so as to obtain a form of expression plasmid of recombinant hK1, denoted as pPICZα-opt-hK1.

(3) Construction of Recombinant hK1 Protein Yeast Engineering Strain

X-33 strains (C18000, purchased from Invitrogen) were prepared as electroporation-competent cells, according to the method in the instruction of Multi-Copy Pichia Expression Kit of Invitrogen Inc. The resultant containing the pPICZα-opt-hK1 plasmid was linearized by enzyme digestion with Sac I restriction endonuclease, and ethanol precipitated, then the linearized vector was electrically transformed into X-33 competent yeast cells, coated onto a YPD solid medium containing Zeocin, and cultured at 30° C. until growth of clones.

(4) Expression of Recombinant hK1 Protein

X-33 positive monoclonal strains of hK1 were picked out, and cultured, in 5 mL BMGY medium, at 30° C. and 220 rpm in a 50-mL sterile centrifuge tube. When $OD_{600}$=3.0-2.0, 1 mL bacterium liquid was taken out to store the strain, and the remaining bacterium liquid was resuspended and then transferred to BMMY for induction and expression in a small amount, and methanol was supplemented every 24 h to a final concentration of 1 wt %. One week later, supernatant of the bacterium liquid was collected by centrifugation.

(5) Expression and Purification of Recombinant hK1 Protein

1. Impurity Removal Pretreatment of Fermentation Liquid

The recombinant hK1 fermentation liquid was centrifuged for 15 min at 12000 rpm and at low temperature, to collect a supernatant. A high-concentration $(NH_4)_2SO_4$ solution was added into the supernatant, and had a final concentration of 1.0 M in the supernatant, and the mixture was filtered through a 0.45-μm filter membrane.

2. HisTrap Phenyl HP Hydrophobic Chromatography

By the optimization of the HisTrap Phenyl HP purification process of the recombinant hK1 fermentation liquid obtained from the pretreatment, through the use of the DOE method in the UNICORN6.1 operational software in a full-automatic intelligent protein purification system (AKTA avant150, purchased from GE heal care), it was finally determined that the equilibration buffer was 20 mM sodium phosphate, 1.0 M $(NH_4)_2SO_4$, 10% glycerin, pH 6.0, and the elution buffer was 20 mM phosphate, 10% glycerin, pH 6.0. The sample was eluted with a gradient concentration of $(NH_4)_2SO_4$ decreased stepwise by 0.2 M. The elution peaks were collected, and the samples separated were identificated by SDS-PAGE. Results are shown in FIG. 10, and two recombinant hK1 proteins with inconsistent molecular weight sizes due to glycosylation modification were separated completely.

Example 11: Protein Electrophoretic Analysis and Activity Determination of PEG Modified Products of Recombinant Human Kallikrein Expressed in Yeasts The recombinant expressed low-molecular weight human kallikrein (hK1K1) from Example 10 was modified with a Y-PALD-30K modifier, and after the modification, a mono-modified product (Y-PALD-30K-hK1K1) was prepared according to the method described in Example 1. Electrophoresis results of the mono-modified product and the original protein are shown in FIG. 11. As can be seen from FIG. 11, the mono-modified product obtained after the purification exhibits a single band, and as compared with the original protein, the molecular weight is increased significantly, up to about 130 KDa. Because PEG can bind to a plethora of water molecules, in electrophoresis the apparent molecular weight thereof will be significantly greater than the actual molecular weight thereof. According to the experimental method in Example 2, the activity of human kallikrein (hK1K1) before and after the modification was determined. Activity determination results indicate that the modified hK1K1 retained 85% of activity of the original protein before modification. Thus it can be seen that, efficacy and pharmacokinetic results of Y-PALD-30K-hK1K1 will also be ameliorated significantly, as compared with the original protein.

Example 12: Preparation of Recombinant Human Kallikrein Expressed in CHO Cells (1) Gene Design According to a sequence of GenBank accession number AAA59455, the gene was subjected to codon optimization, to obtain a recombinant hK1 gene according to the present invention, as shown in SEQ ID No: 4.

(2) Construction of Expression Plasmid of Recombinant hK1 Gene

The fragment synthesized from the optimized recombinant hK1 full gene was constructed into pUC57 plasmids (provided by Nanjing Genscript Biotechnology Co., LTD.), to obtain a long-term storage plasmid, denoted as pUC57-opt-hK1 plasmid.

The pUC57-opt-hK1 plasmid was used as a template, and upstream primer P3 was introduced into Avrll and downstream primer P4 was introduced into BstZ171 restriction enzyme cutting sites, to perform PCR amplification. The primers employed had sequences as follows:

```
Upstream primer P3:
                                    SEQ ID NO: 7
CATGCCTAGGGCCACCATGTCCGCTCTGCT Downstream primer P4:
                                    SEQ ID NO: 8
GGGCGTATACTCAACTGTTTTCAGCAATGGT
```

The total reaction volume was 50 μL, where 2.5 μL each of the primers at a concentration of 10 μmol/L was added, 1 μL of dNTP at a concentration of 10 mmol/L was added, and 0.5 μL of DNA polymerase employed, which was Q5 High-Fidelity DNA Polymerase, at 2 U/μL, was added. Reaction condition included 98° C. for 10 s, 55° C. for 20 s, and 72° C. for 30 s. After 25 cycles, the product was analyzed by 1.0% agarose gel electrophoresis, and the size of the product was consistent with the expected size (780 bp, as shown in FIG. 7). The obtained gene product was purified by a DNA gel recovery kit. After the purification, with Avrll (R0104S, purchased from New England Biolabs) and BstZ171 (R0136S, purchased from New England Biolabs), it was linked to pCHO1.0 plasmid (A1369601, purchased from Invitrogen) by T4 ligase, transformed into Top 10 competent cells (CB104, purchased from Beijing Tiangen Biotech), and cultured overnight at 37° C. in an LB flat plate containing kanamycin (0408-100G, purchased from Amresco). The next day, positive clone bacteria were screened, sequenced, and aligned, to be completely identical with the expected sequence, so as to obtain a form of expression plasmid of recombinant hK1, denoted as pCHO1.0-opt-hK1.

(3) Preparation of CHO Positive Clones

An appropriate amount of CHO-S (A1369601, purchased from Invitrogen) cells were added into a 24-well plate respectively, followed by the addition of CD FortiCHO (A1148301, purchased from Invitrogen) medium with various concentrations of puromycin successively. 2 weeks later, the working concentration of puromycin was determined, by the MTT method, to be between 5 and 10 µg/mL. In this application, the working concentration of puromycin was initially 10 µg/mL.

Correctly sequenced pCHO1.0-opt-hK1 plasmids were linearized by NruI (R0192S, purchased from Invitrogen), electrically transfected into CHO-S cells, then puromycin and MTX were added therein respectively to perform screening, and cell viability was calculated after one week. When the cell viability was greater than 30%, the plasmids were transferred to a shaker, and pressurized screening was performed by continuously increasing the puromycin and MTX concentrations, until the expression amount evaluation was passed. Monoclonal cell strains were screened by a limiting dilution method, and high-expression cell strains were identified by protein immunoblotting.

(4) Expression of Recombinant hK1 in Mammal Cell CHO

Monoclonal cell strains CHO-S expressing recombinant hK1 were inoculated into a CD FortCD medium, and cultured in a shaker at 37° C., 8% $CO_2$, and 130 rpm. When the cell density satisfied the requirement, 2 g/L glucose was sequentially added every other day, and samples were taken, to detect the viability and density of the cells. When the cell viability was lower than 70%, the medium containing recombinant human kallikrein was collected. Glucose was sequentially added everyday, and the supernatant culture solution was collected for identification by immunoblotting maps, with results shown in FIG. 12. Experimental results show that, CHO-S can express the recombinant hK1 protein with high efficiency, and due to the different sugar modification, the recombinant hK1 protein has relatively broad molecular weight distribution.

Example 13: HPLC Analysis and Activity Determination of PEG Modified Products of Recombinant Human Kallikrein Expressed in CHO Cells The recombinant human kallikrein expressed in CHO cells prepared in Example 12 was modified with a Y-PALD-30K modifier, and after the modification, a mono-modified product (Y-PALD-30K-rhK1K1) was prepared according to the method described in Example 1. HPLC analytic results of the mono-modified product are shown in FIG. 13. As can be seen from FIG. 13, the mono-modified product obtained after the purification has higher purity, up to more than 98%. Also, the peak position is apparently-left shifted as compared with the original protein, indicating that its molecular weight is significantly increased after the PEG modification. According to the experimental method in Example 2, the activity of human kallikrein before and after the modification was determined. Activity determination results indicate that the modified rhK1K1 retains 88% of activity of the original protein, which is also similar to the results in Examples 2 and 11. Thus it can be seen that, efficacy and pharmacokinetic results of Y-PALD-30K-rhK1K1 will also be ameliorated significantly, as compared with the original protein.

The above examples are only used for illustrating the technical conception and feature of the present invention, for the purpose of enabling those familiar in the art to understand and thereby implement the content of the present invention, instead of limiting the protection scope of the present invention therewith. Any equivalent changes or modifications made according to the spirit and essence of the present invention shall all be encompassed within the protection scope of the present invention.

What is claimed is:

1. A PEGylated tissue kallikrein, wherein the PEGylated tissue kallikrein by has the structural formula (I):

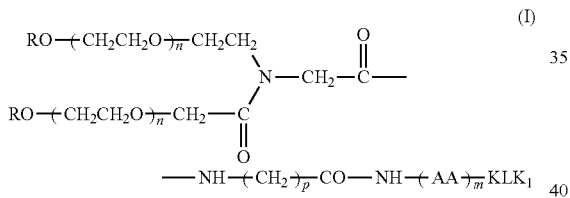

wherein R is H or $C_1$-$C_4$ alkyl; n is an integer between 10 and 455, p is an integer from 1 to 3; AA is an N-terminal L-amino acid residue, KLK1 has an amino acid sequence of SEQ ID No. 1 or SEQ ID No. 2; and m is an integer from 0 to 5; and the molecular weight of the following moiety of (I):

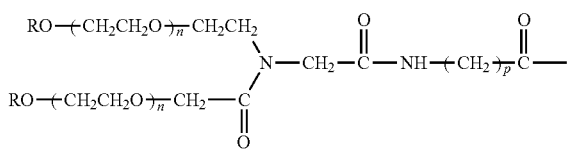

is 20 kDa to 30 kDa.

2. The PEGylated tissue kallikrein according to claim 1, wherein p is 2.

3. The PEGylated tissue kallikrein according to claim 1, wherein the alkyl is methyl, p is 2, and m is 0.

4. A method for preparing the PEGylated tissue kallikrein (I) according to claim 1, comprising:

step 1: formulating a 0.1-30 mg/mL tissue kallikrein solution with a 10-50 mM sodium acetate buffer having a pH 4-6;

step 2: reacting for 0.1 to 24 h at 4 to 37° C. at a molar ratio of tissue kallikrein:PEG:reductant=1: (2-25): (20-1000); and step 3: purifying by chromatography after reaction, to obtain a mono-PEGylated tissue kallikrein;

wherein, the reductant is sodium cyanoborohydride, and PEG has the structural formula (II):

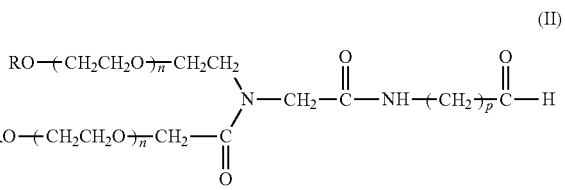

wherein R is H or $C_1$-$C_4$ alkyl; n is an integer between 10 and 455, p is an integer from 1 to 3; AA is an N-terminal L-amino acid residue, KLK1 has an amino acid sequence of SEQ ID No. 1 or SEQ ID No. 2; and m is an integer from 0 to 5; and the molecular weight of (II) is 20 kDa to 30 kDa.

5. A method for treating cerebral apoplexy or diabetic neuropathy comprising administering, to a patient in need thereof, a drug comprising the PEGylated tissue kallikrein according to claim 1.

6. A drug for treating cerebral apoplexy or diabetic nephropathy, comprising the PEGylated tissue kallikrein according to claim 1 or a pharmaceutically acceptable salt thereof, as an active ingredient.

* * * * *